United States Patent
Schwab et al.

(10) Patent No.: US 9,550,678 B2
(45) Date of Patent: Jan. 24, 2017

(54) POLYMERIC PRECURSORS FOR PRODUCING GRAPHENE NANORIBBONS AND METHODS FOR PREPARING THEM

(71) Applicants: BASF SE, Ludwigshafen (DE); Max-Planck-Gesellschaft zur Foerderung der Wissenschaften e. V., Munich (DE)

(72) Inventors: Matthias Georg Schwab, Mannheim (DE); Akimitsu Narita, Mainz (DE); Xinliang Feng, Mainz (DE); Klaus Muellen, Cologne (DE)

(73) Assignees: BASF SE, Ludwigshafen (DE); Max-Planck-Gesellschaft zur Förderung der Wissenschaften e.V., Munich (DE)

(*) Notice: Subject to any disclaimer, the term of this patent is extended or adjusted under 35 U.S.C. 154(b) by 71 days.

(21) Appl. No.: 14/367,041

(22) PCT Filed: Dec. 17, 2012

(86) PCT No.: PCT/IB2012/057377
§ 371 (c)(1),
(2) Date: Jun. 19, 2014

(87) PCT Pub. No.: WO2013/093756
PCT Pub. Date: Jun. 27, 2013

(65) Prior Publication Data
US 2014/0353554 A1    Dec. 4, 2014

Related U.S. Application Data

(60) Provisional application No. 61/577,689, filed on Dec. 20, 2011.

(51) Int. Cl.
C01B 31/04    (2006.01)
C07C 49/683    (2006.01)
(Continued)

(52) U.S. Cl.
CPC ............ C01B 31/0446 (2013.01); B82Y 30/00 (2013.01); B82Y 40/00 (2013.01); C07C 49/683 (2013.01);
(Continued)

(58) Field of Classification Search
None
See application file for complete search history.

(56) References Cited

U.S. PATENT DOCUMENTS 7,381,850 B2    6/2008  Godschalx et al.
2005/0067955 A1*   3/2005  Cho ..................... C07C 13/567
                                        313/510
(Continued)

FOREIGN PATENT DOCUMENTS

WO    WO 2004/089862 A2    10/2004
WO    WO 2009/101449 A2    8/2009
(Continued)

OTHER PUBLICATIONS

Morgenroth, F. et al., "Dendritic and Hyperbranched Polyphenylenes via a simple Diels-Alder route," Tetrahedron, 53(45), pp. 15349-15366 (1997).*

(Continued)

Primary Examiner — Mark Kopec
Assistant Examiner — Jaison Thomas
(74) Attorney, Agent, or Firm — Oblon, McClelland, Maier & Neustadt, L.L.P.

(57) ABSTRACT

An oligophenylene monomer of general formula (I) wherein $R^1$ and $R_2$ are independently of each other H, halogene, —OH, —NH$_2$, —CN, —NO$_2$ or a linear or branched, saturated or unsaturated $C_1$-$C_{40}$ hydrocarbon residue, which can be substituted 1-to 5-fold with halogene (F, Cl, Br, I), —OH, —NH$_2$, —CN and/or —NO$_2$, and wherein one or
(Continued)

more $CH_2$-groups can be replaced by —O— or —S—, or an optionally substituted aryl, alkylaryl or alkoxyaryl residue; and m represents 0, 1 or 2.

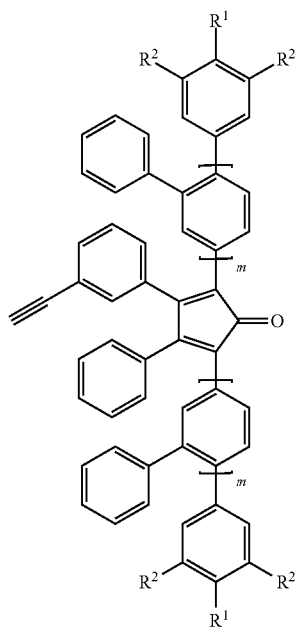

(I)

12 Claims, 5 Drawing Sheets

(51) Int. Cl.

| C08F 138/00 | (2006.01) |
|---|---|
| H01B 1/04 | (2006.01) |
| C08F 2/00 | (2006.01) |
| B82Y 30/00 | (2011.01) |
| B82Y 40/00 | (2011.01) |
| C08G 61/10 | (2006.01) |
| C08L 65/00 | (2006.01) |

(52) U.S. Cl.
CPC ............... *C08F 2/00* (2013.01); *C08F 138/00* (2013.01); *C08G 61/10* (2013.01); *C08L 65/00* (2013.01); *H01B 1/04* (2013.01); *C08G 2261/1412* (2013.01); *C08G 2261/312* (2013.01); *C08G 2261/364* (2013.01); *C08G 2261/46* (2013.01); *C08G 2261/91* (2013.01); *C08G 2261/92* (2013.01); *C08G 2261/95* (2013.01); *Y10S 977/734* (2013.01); *Y10S 977/842* (2013.01); *Y10S 977/932* (2013.01)

(56) References Cited

U.S. PATENT DOCUMENTS

| 2007/0181961 | A1 | 8/2007 | Marks et al. | |
| 2010/0038629 | A1* | 2/2010 | Lazarev | B82Y 10/00 |
| | | | | 257/29 |
| 2010/0105834 | A1 | 4/2010 | Tour et al. | |
| 2012/0197051 | A1 | 8/2012 | Tour et al. | |

FOREIGN PATENT DOCUMENTS

| WO | WO 2010/147860 A1 | 12/2010 | | |
| WO | WO 2010147860 A1 * | 12/2010 | ............ | B82Y 30/00 |
| WO | WO 2011/112589 A1 | 9/2011 | | |

OTHER PUBLICATIONS

Office Action issued Jun. 26, 2015 in Chinese Patent Application No. 201280062060.2 (submitting English language translation only).
International Search Report issued May 23, 2013, in PCT/IB12/057377 filed Dec. 17, 2012.
Written Opinion of the International Searching Authority issued May 23, 2013, in PCT/IB12/057377 filed Dec. 17, 2012.
Mihov, et al., "Toward Nanoamphiphiles: Efficient Synthesis of Desymmetrized Polyphenylene Dendrimers", JOCArticle, J. Org. Chem., vol. 69, Oct. 20, 2004, pp. 8029-8037.
Treier, et al., "Surface-assisted cyclodehydrogenation provides a synthetic route towards easily processable and chemically tailored nanographenses", Nature Chemistry, vol. 3, Nov. 7, 2010, pp. 61-67.
Wu, et al., "From Branched Polyphenylenes to Graphite Ribbons", Macromolecules, vol. 36, 2003, pp. 7082-7089.
Yang, et al., "Two-Dimensional Graphene Nanoribbons", J. Am. Chem. Soc., vol. 130, 2008, 21 pages.
Fogel, et al., "Graphitic Nanoribbons with Dibenso[e,l]pyrene Repeat Units: Synthesis and Self-Assembly", Macromolecules, vol. 42, 2009, pp. 6878-6884.
Zinaida B. Shifrina, et al., "Branched Polyphenylenes by Repetitive Diels-Alder Cycloaddition" Macromolecules, vol. 33, No. 10, XP055185572, 2000, pp. 3525-3529.

* cited by examiner

| Detector | Mn (g/mol) | Mw (g/mol) | D (Mw/Mn) | Vp (ml) | Mp (g/mol) | Area (ml*V) |
|---|---|---|---|---|---|---|
| UV S3702 | 121855,00 | 217135,00 | 1,78 | 21,63 | 115150,00 | 0,28 |
| RI 101 | 108449,00 | 205598,00 | 1,90 | 21,70 | 110780,00 | 0,00 |

POLYMERIC PRECURSORS FOR PRODUCING GRAPHENE NANORIBBONS AND METHODS FOR PREPARING THEM

CROSS REFERENCE TO RELATED APPLICATION

This application is a 371 of PCT/IB2012/057377, filed on Dec. 17, 2012, and claims the benefit of U.S. Provisional Application No. 61/577,689, filed on Dec. 20, 2011.

The present invention concerns polymeric precursors for producing graphene nanoribbons, methods for preparing them, and oligophenylene monomers for the synthesis of polymeric precursors, as well as methods for preparing the graphene nanoribbons from the polymeric precursors and the oligophenylene monomers.

Graphene, an atomically thin layer from graphite, has received considerable interest in physics, material science and chemistry since the recent discovery of its appealing electronic properties. These involve superior charge carrier mobility and the quantum Hall effect. Moreover, its chemical robustness and material strength make graphene an ideal candidate for applications ranging from transparent conductive electrodes to devices for charge and energy storage.

Graphene nanoribbons (GNRs) are linear structures that are derived from the parent graphene lattice. Their characteristic feature is high shape-anisotropy due to the increased ratio of length over width. Currently, their usage in yet smaller, flatter and faster carbon-based devices and integrated circuits is being widely discussed in material science. In contrast to graphene, armchair-type GNRs exhibit a band gap that can be adjusted by their width. Their length becomes relevant when GNRs are to be used in devices such as field-effect transistors (FETs) for which a minimum channel width has to be bridged. The same holds for the potential replacement of copper or gold in nanoscale conducting pathways. At the same time the edge structure of the GNRs will have a strong impact. Computational simulations and experimental results on smaller nanographenes suggest that GNRs exhibiting nonbonding π-electron states at zigzag edges could be used as active component in spintronic devices.

Because considerable complexity governs design, chemical preparation and processing of chemically defined GNRs, only very few of these structures are known. In the recent past, only a limited number of synthetic attempts have been published addressing the fabrication of GNRs of defined geometry, width, length, edge structure and heteroatom-content. Based on the reaction environment the studies on the synthetic bottom-up fabrication of GNRs can be further divided into solution- and surface-based routes.

For solution-based approaches using oligophenylene precursors a polymer is typically prepared in a first step which is subsequently converted into the graphitic structure by Scholl-type oxidative cyclodehydrogenation. However, the design of the parent monomer must be carefully adjusted in order to guarantee for a suitable arrangement of the aromatic units upon the chemistry-assisted graphitization into the final GNR structure.

J. Wu, L. Gherghel, D. Watson, J. Li, Z. Wang, C. D. Simpson, U. Kolb, and K. Müllen, Macromolecules 2003, 36, 7082-7089 report the synthesis of graphitic nanoribbons obtained by intramolecular oxidative cyclodehydrogenation of soluble branched polyphenylenes, which were prepared by repetitive Diels-Alder cycloaddition of 1,4-bis(2,4,5-triphenylcyclopentadienone-3-yl)benzene and diethynylterphenyl. The obtained graphene ribbons are not linear but rather contain statistically distributed "kinks" due to the structural design of the polyphenylene precursor.

X. Yang., X. Dou, A. Rouhanipour, L. Zhi, H. J. Räder, and K. Müllen, JACS Communications, published on Web Mar. 7, 2008, report the synthesis of two-dimensional graphene nanoribbons. Suzuki-Miyaura coupling of 1,4-diiodo-2,3,5,6-tetraphenylbenzene with 4-bromophenylboronic acid gives dibromo-hexaphenylbenzene, which is converted into the bis-boronic ester. Suzuki-Miyaura polymerization of the bis-boronic ester with diiodobenzene furnished polyphenylenes in a strongly sterically hindered reaction. Intramolecular Scholl reaction of the polyphenylene with $FeCl_3$ as oxidative reagent provides graphene nanoribbons.

Y. Fogel, L. Zhi, A. Rouhanipour, D. Andrienko, H. J. Räder, and K. Müllen, Macromolecules 2009, 42, 6878-6884 report the synthesis of a homologous series of five monodisperse ribbon-type polyphenylenes, with rigid dibenzopyrene cores in the repeat units, by microwave-assisted Diels-Alder reaction. The size of the obtained polyphenylene ribbons ranges from 132 to 372 carbon atoms in the aromatic backbone which incorporates up to six dibenzopyrene units. Because of the flexibility of the backbone and the peripheral substitution with dodecyl chains, the polyphenylene ribbons are soluble in organic solvents. In a further reaction step, ribbon-type polycyclic aromatic hydrocarbons (PAHs) are prepared by cyclodehydrogenation.

All three methods suffer from drawbacks regarding the final graphene nanoribbon.

In the first case, the resulting graphene nanoribbons are ill-defined due to the statistically arranged "kinks" in their backbone. Furthermore the molecular weight is limited due to the sensitivity of the A2B2-type polymerization approach to aberrations fromstoichiometry. No lateral solubilizing alkyl chains have been introduced into the graphene nanoribbons.

The second case suffers also from the stoichiometry issue due to the underlying A2B2-stoichiometry of the A2B2-type Suzuki protocol and the sterical hindrance of 1,4-diiodo-2,3,5,6-tetraphenylbenzene.

The third case makes use of a step-wise synthesis which provides very defined cut-outs from graphene nanoribbons but is impracticable for the fabrication of high-molecular weight species.

It is an object of the present invention to provide new methods for the production of graphene nanoribbons. It is a further object of the present invention to provide suitable polymeric precursors for producing graphene nanoribbons, as well as methods and suitable oligophenylene monomers for preparing such polymeric precursors.

The problem is solved by a oligophenylene monomer of general formula (I),

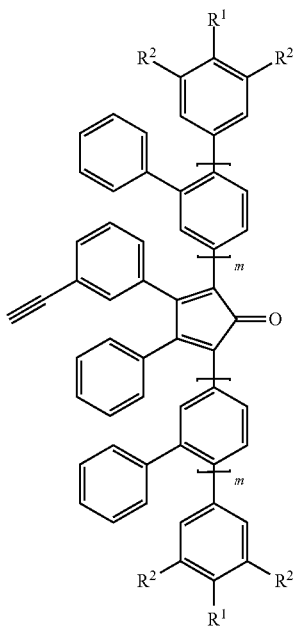

(I)

wherein
R¹ and R² are independently of each other H, halogene, —OH, —NH₂, —CN, —NO₂ or a linear or branched, saturated or unsaturated $C_1$-$C_{40}$ hydrocarbon residue, which can be substituted 1- to 5-fold with halogene (F, Cl, Br, I), —OR³, —NR³₂, —CN and/or —NO₂, and
wherein one or more CH₂-groups can be replaced by —O—, —S—, —NR⁴—, —OC(O)— or —C(O)—, or an optionally substituted aryl, alkylaryl or alkoxyaryl residue;

each R³ is independently of each other H, $C_1$-$C_{30}$ alkyl, $C_2$-$C_{30}$ alkenyl, $C_2$-$C_{30}$ alkynyl, $C_1$-$C_{30}$ haloalkyl, $C_2$-$C_{30}$ haloalkenyl, $C_2$-$C_{30}$ haloalkynyl or $C_2$-$C_{30}$ acyl;
each R⁴ is independently of each other H, $C_1$-$C_{30}$ alkyl, $C_2$-$C_{30}$ alkenyl, $C_2$-$C_{30}$ alkynyl, $C_1$-$C_{30}$ haloalkyl, $C_2$-$C_{30}$ haloalkenyl, $C_2$-$C_{30}$ haloalkynyl or $C_2$-$C_{30}$ acyl; and m represents 0, 1 or 2.

Preferably, R¹ and R² are independently of each other H, $C_1$-$C_{30}$ alkyl, $C_1$-$C_{30}$ alkoxy, $C_1$-$C_{30}$ alkylthio, $C_2$-$C_{30}$ alkenyl, $C_2$-$C_{30}$ alkynyl, $C_1$-$C_{30}$ haloalkyl, $C_2$-$C_{30}$ haloalkenyl or haloalkynyl, e.g. $C_1$-$C_{30}$ perfluoroalkyl. More preferably R¹ and R² are independently of each other H, $C_1$-$C_{30}$ alkyl or $C_1$-$C_{30}$ alkoxy. Most preferably R¹ and R² and are independently of each other H or $C_1$-$C_{30}$ alkyl.

$C_1$-$C_{30}$ alkyl can be linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl.

$C_1$-$C_{30}$ alkoxy groups are straight-chain or branched alkoxy groups, e.g. methoxy, ethoxy, n-propoxy, isopropoxy, n-butoxy, sec-butoxy, tert-butoxy, amyloxy, isoamyloxy, tert-amyloxy, heptyloxy, octyloxy, isooctyloxy, nonyloxy, decyloxy, undecyloxy, dode-cyloxy, tetradecyloxy, pentadecyloxy, hexadecyloxy, heptadecyloxy or octadecyloxy.

The term "alkylthio group" means the same groups as the alkoxy groups, except that the oxygen atom of the ether linkage is replaced by a sulfur atom.

$C_2$-$C_{30}$ alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-30}$ alkynyl is straight-chain or branched and may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1l-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{30}$-perfluoroalkyl is a branched or unbranched radical such as for example —CF₃, —CF₂CF₃, —CF₂CF₂CF₃, —CF(CF₃)₂, —(CF₂)₃CF₃ or —C(CF₃)₃.

The terms "haloalkyl, haloalkenyl and haloalkynyl" mean groups given by partially or wholly substituting the above-mentioned alkyl group, alkenyl group and alkynyl group with halogen.

$C_2$-$C_{30}$ acyl is straight-chain or branched and may be saturated or unsaturated, such as, for example, ethanoyl, propanoyl, isobutanoyl, n-butanoyl, pentanoyl, hexanoyl, heptanoyl, octanoyl, nonanoyl, decanoyl or dodecanoyl.

Aryl is usually $C_6$-$C_{30}$ aryl, which optionally can be substituted, such as, for example, phenyl, 4-methylphenyl, 4-methoxyphenyl, naphthyl, biphenylyl, terphenylyl, pyrenyl, fluorenyl, phenanthryl, anthryl, tetracyl, pentacyl or hexacyl.

In a preferred embodiment of the invention, R¹ is a linear or branched $C_1$-$C_{30}$ alkyl and R² is H.

The problem is further solved by a polymeric precursor for producing graphene nanoribbons having repeating units of general formula (II),

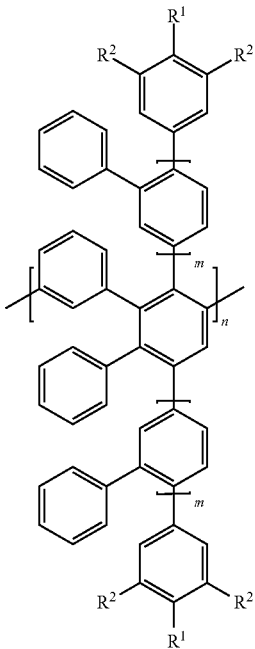

(II)

wherein
R¹ and R² are independently of each other H, halogene, —OH, —NH₂, —CN, —NO₂ or a linear or branched, saturated or unsaturated $C_1$-$C_{40}$ hydrocarbon residue, which can be substituted 1- to 5-fold with halogene (F, Cl, Br, I), —OR³, —NR³₂, —CN and/or —NO₂, and wherein one or more CH₂-groups can be replaced by —O—, —S—, —NR⁴—, —OC(O)— or —C(O)—, or an optionally substituted aryl, alkylaryl or alkoxyaryl residue;

each $R^3$ is independently of each other H, $C_1$-$C_{30}$ alkyl, $C_2$-$C_{30}$ alkenyl, $C_2$-$C_{30}$ alkynyl, $C_1$-$C_{30}$ haloalkyl, $C_2$-$C_{30}$ haloalkenyl, $C_2$-$C_{30}$ haloalkynyl or $C_2$-$C_{30}$ acyl;
each $R^4$ is independently of each other H, $C_1$-$C_{30}$ alkyl, $C_2$-$C_{30}$ alkenyl, $C_2$-$C_{30}$ alkynyl, $C_1$-$C_{30}$ haloalkyl, $C_2$-$C_{30}$ haloalkenyl, $C_2$-$C_{30}$ haloalkynyl or $C_2$-$C_{30}$ acyl;
m represents 0, 1 or 2; and
n represents a number of from 2 to 900.

Preferably, $R^1$ and $R^2$ are independently of each other H, $C_1$-$C_{30}$ alkyl, $C_1$-$C_{30}$ alkoxy, $C_1$-$C_{30}$ alkylthio, $C_2$-$C_{30}$ alkenyl, $C_2$-$C_{30}$ alkynyl, $C_1$-$C_{30}$ haloalkyl, $C_2$-$C_{30}$ haloalkenyl or haloalkynyl, e.g. $C_1$-$C_{30}$ perfluoroalkyl. More preferably $R^1$ and $R^2$ are independently of each other H, $C_1$-$C_{30}$ alkyl or $C_1$-$C_{30}$ alkoxy. Most preferably $R^1$ and $R^2$ are independently of each other H or $C_1$-$C_{30}$ alkyl.

Preferably, $R^2$ in formulae (I) and (II) is H.

Preferably, m in formulae (I) and (II) represents 0 or 1. More preferably, m in formulae (I) and (II) represents 0.

In a preferred embodiment of the invention, $R^1$ is a linear or branched $C_1$-$C_{30}$ alkyl and $R^2$ is H.

The oligophenylene monomer of general formula (I) is used for the preparation of the polymeric precursor for producing graphene nanoribbons having repeating units of general formula (II) by reacting it via Diels-Alder-Reaction according to Scheme 1.

The Diels-Alder reaction represents a well-established protocol which has been used for the build-up of functional molecules and polymers. The Diels-Alder-Reaction of oligophenylene monomer of general formula (I) to the polymeric precursor having repeating units of general formula (II) can be achieved under different conditions. For example, the Diels-Alder-Reaction can be performed in high boiling solvents at elevated temperatures. Suitable high boiling solvents are diphenyl ether, 1,1,2,2-tetrachloroethane, 1,2-dichlorobenzene, 1,2,4-trichlorobenzene, nitrobenzene and benzophenone.

Alternatively, the Diels-Alder-Reaction can be performed without using solvents at temperatures between 200° C. and 300° C.

Scheme 1

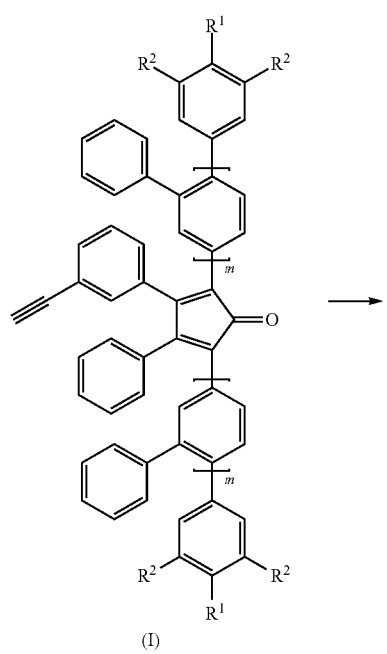

(I)

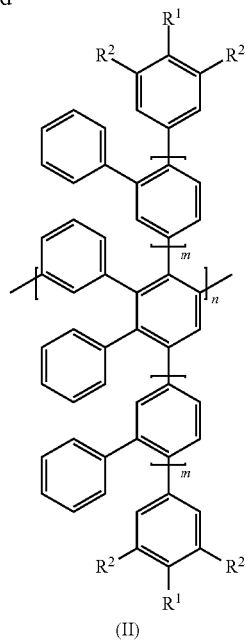

(II)

In general, the polymeric precursor having repeating units of general formula (II) contains from 2 to 900 repeating units and has a molecular weight of from 1 000 to 600 000 g/mol.

The invention also concerns a process for the preparation of the polymeric precursor having repeating units of general formula (II) by Diels-Alder polymerization of the oligophenylene monomer of general formula (I).

The invention also concerns a process for the preparation of graphene nanoribbons by cyclodehydrogenation of the polymeric precursor having repeating units of general formula (II) according to Scheme 2.

The preparation of graphene nanoribbons of general formula (III) from the polymeric precursor having repeating units of general formula (II) can be performed e.g. using ferric(III) chloride as oxidant in a mixture of DCM and nitromethane (Scheme 2). Depending on the temperature and the nature of the polymeric precursor having repeating units of general formula (II), the reaction time is from 2 h to 10 d. If the reaction is carried out at around 20° C., the reaction time is usually between two and four days. Preferably, a stream of an inert gas is passed through the reaction mixture during the reaction to avoid side reactions.

Alternatively, the preparation of graphene nanoribbons of general formula (III) can be carried out using phenyliodine (III)bis(trifluoroacetate) (PIFA) and boron trifluoride etherate in anhydrous DCM or molybdenum(V) pentachloride in anhydrous DCM.

In general, the molecular weight of the graphene nanoribbons of general formula (III) varies from 1 000 to 600 000 g/mol.

Scheme 2

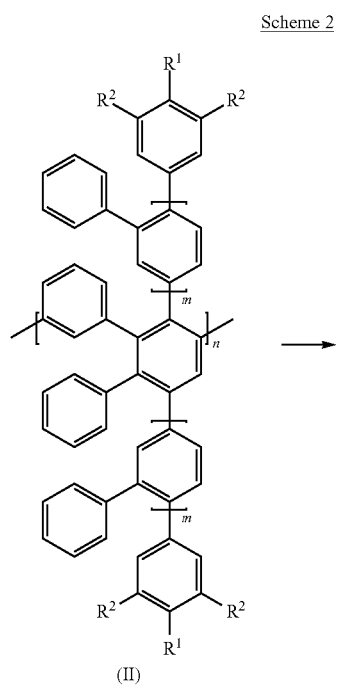

(II)

The oligophenylene monomer of general formula (I) can be synthesized according to Schemes 3 to 7 below, involving the two intermediates 3-bromobenzil 4 and substituted 1,3-bis(oligophenylenyl)propan-2-one 8, as summarized below in Scheme 7. The reaction conditions and solvents used are purely illustrative, of course other conditions and solvents can also be used and will be determined by the skilled in the art. Depending on the desired width of the graphene nanoribbons of general formula (III), different substituted 1,3-bis(oligophenylenyl)propan-2-ones 8 (m=0, 1 or 2) can be reacted with 3-bromobenzil 4. Suitable substituted 1,3-bis(oligophenylenyl)propan-2-ones 8 are for example the 1,3-bis(oligophenylenyl)propan-2-ones 8-0 with m=0 (Scheme 4), 8-1 with m=1 (Scheme 5) and 8-2 with m=2 (Scheme 6).

In a first reaction sequence, the intermediate 3-bromobenzil 4 can be synthesized via a two-step route from commercially available 1-bromo-3-iodobenzene 1 and ethynylbenzene 2 (Scheme 3). Sonogashira-type coupling of 1 and 2 can be used for the build-up of 3-bromodiphenylacetylene 3. The reaction can be achieved in a mixture of THF and triethylamine at room temperature in the presence of copper (I) iodide and a palladium(II) catalyst. Due to the higher reactivity of the iodine carbon bond of 1-bromo-3-iodobenzene 1, the coupling only proceeded at the desired 3-position.

The second step consists in the oxidation of the acetylene group of 3-bromodiphenylacetylene 3 to yield the 3-bromobenzil 4. This step can be realized by stirring bromodiphenylacetylene 3 in the presence of iodine in dimethyl sulfoxide at elevated temperatures.

Scheme 3

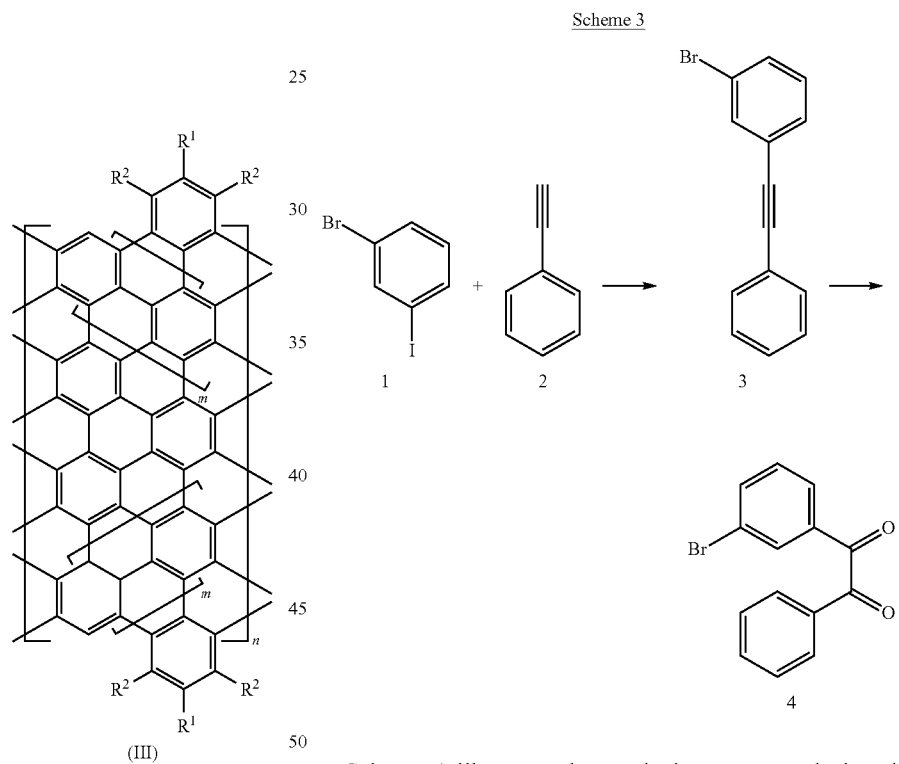

Scheme 4 illustrates the synthetic route to substituted 1,3-bis(oligophenylenyl)propan-2-one 8-0 starting from literature known halogenated toluene 5, wherein X and Y are independently selected from Cl, Br, I or H. The first step consists in the bromination of the benzylic position of halogenated toluene 5 to yield the halogenated benzyl bromide 6. This step can be realized by heating halogenated toluene 5 under reflux in carbon tetrachloride in the presence of N-bromosuccinimide (NBS) and benzoyl peroxide. The halogenated benzyl bromide 6 can be further reacted to the halogenated 1,3-bis(phenyl)propan-2-one 7. This is achieved by heating the halogenated benzyl bromide 6 under reflux in a reaction mixture of dichloromethane and water using iron(0) pentacarbonyl, potassium hydroxide and benzyltriethylammonium chloride. The last reaction step of this reaction sequence can be carried out with any desired substituted or non-substituted halide R¹X' or R²X', wherein X' is selected from Cl, Br or I and $R^1$ and $R^2$ are as defined above. For example, substituted 1,3-bis(oligophenylenyl)propan-2-one 8-0 is accessible using zinc(II) iodide and a palladium(0) catalyst at room temperature. If both X and Y are H, this reaction step is omitted.

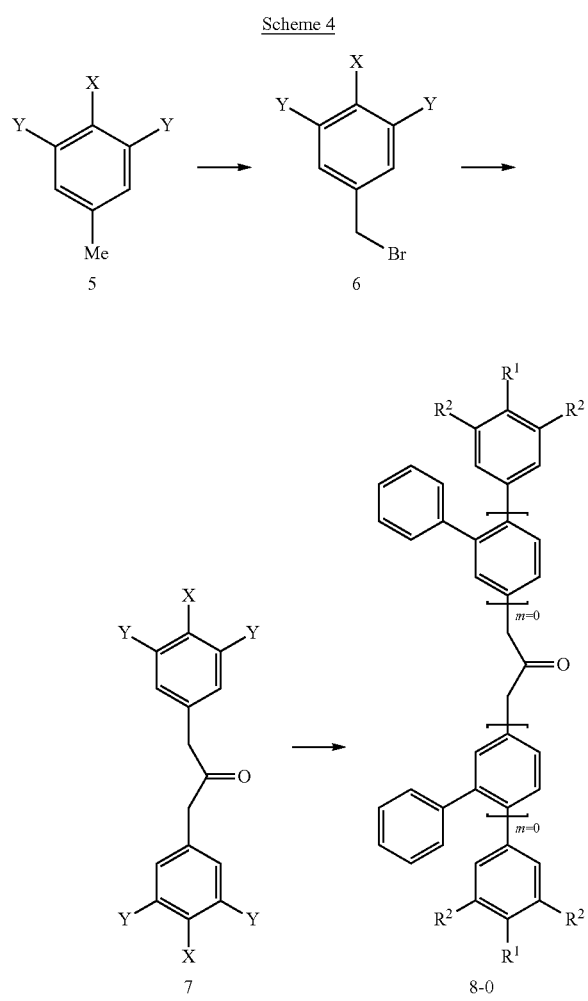

The synthesis of substituted 1,3-bis(oligophenylenyl)propan-2-one 8-1 (m=1) is shown in Scheme 5. Substituted 1,3-bis(oligophenylenyl)propan-2-one 8-1 can be synthesized via a four step route starting from commercially available 2-bromo-1-iodo-5-methylbenzene 9 and phenylboronic acid 10. Suzuki cross coupling of 9 and 10 can be used for the build-up of the 2-bromo-5-methyl-biphenyl 11. The reaction can be achieved at an elevated temperature in a reaction mixture of toluene, ethanol and water in the presence of potassium carbonate and catalytic amounts of tetrakis(triphenylphosphine)palladium(0). Due to the higher reactivity of the iodine carbon bond, the coupling mainly proceeds at the iodine atom in the desired 1-position. The next step consists in the bromination of the benzylic position of 2-bromo-5-methyl-biphenyl 11 to yield the functionalized biphenyl 12. This step can be realized by heating bromo-5-methyl-biphenyl 11 under reflux in carbon tetrachloride using N-bromosuccinimide (NBS) and benzoyl peroxide.

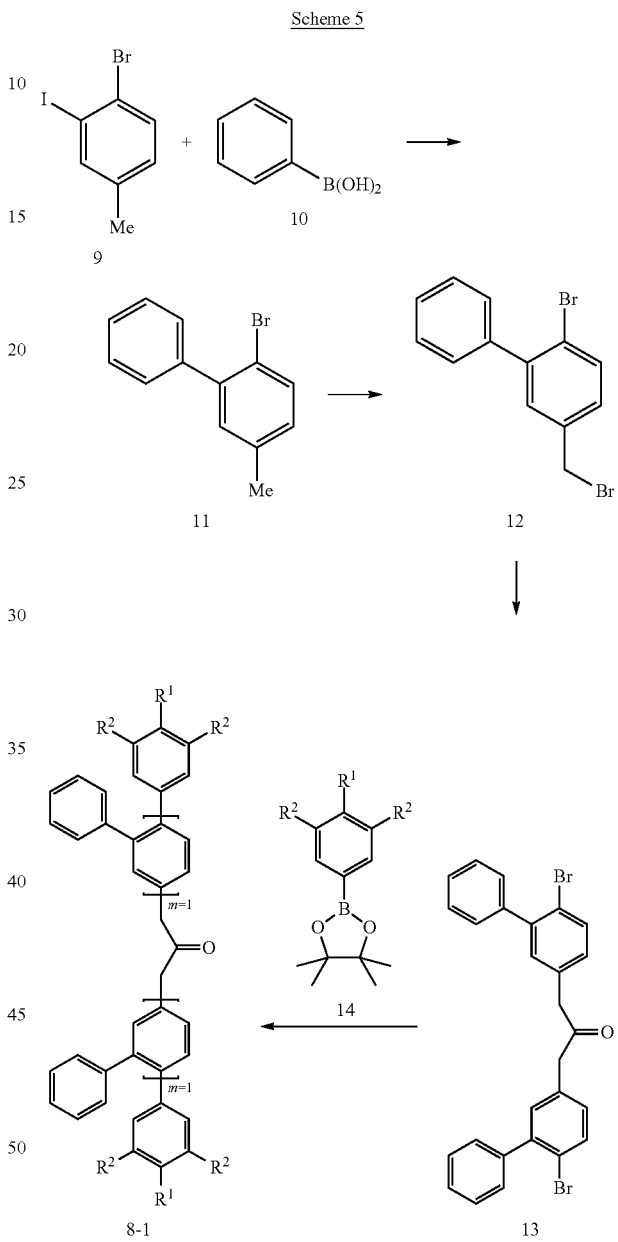

The functionalized biphenyl 12 can be further reacted to 1,3-bis(bromobiphenyl)propan-2-one 13. This is achieved by boiling the functionalized biphenyl 12 in a reaction mixture of dichloromethane and water in the presence of iron(0) pentacarbonyl, potassium hydroxide and benzyltriethylammonium chloride. In the last step, Suzuki cross coupling of 1,3-bis(bromobiphenyl)propan-2-one 13 with arylboronic acid pinacol ester 14 in the presence of potassium carbonate and of tetrakis(triphenyl-phosphine)palladium(0) yields the substituted 1,3-bis(oligophenylenyl)propan-2-one 8-1 (m=1). $R^1$ and $R^2$ are as defined above.

The synthesis of substituted 1,3-bis(oligophenylenyl)propan-2-one 8-2 (m=2) is shown in Scheme 6. The synthesis of the substituted 1,3-bis(oligophenylenyl)propan-2-one 8-2 starts from commercially available 2-bromo-4-chloro-1-iodobenzene 16 and the afore mentioned substituted phenylboronic acid pinacol ester 14. Suzuki cross coupling can be used for the build-up of the substituted 2-bromo-4-chlorobiphenyl 17. The reaction can be performed e.g. at an elevated temperature in a reaction mixture of toluene, ethanol and water in the presence of potassium carbonate and of tetrakis(triphenylphosphine)palladium(0). Preferably, exactly 1.00 equivalent of substituted phenylboronic acid pinacol ester 14 is used. Subsequently, the 2-bromo-4-chlorobiphenyl 17 is converted with phenylboronic acid 10 in a second Suzuki reaction to yield the substituted chlorotrisphenylene 18. The conditions applied are the same as in the step before but at a higher temperature.

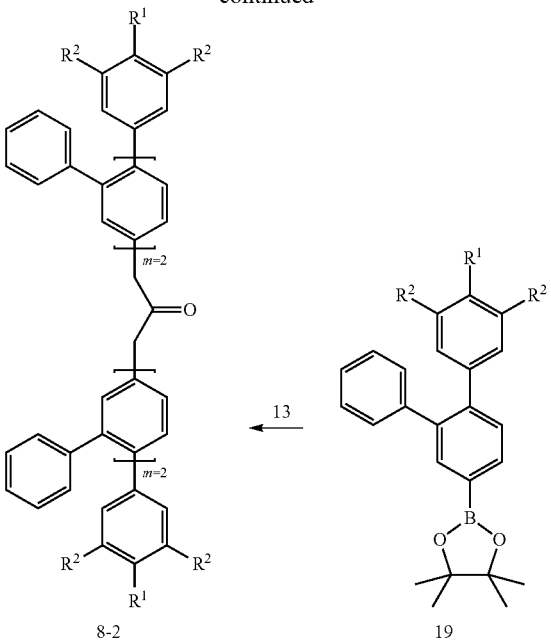

Scheme 6

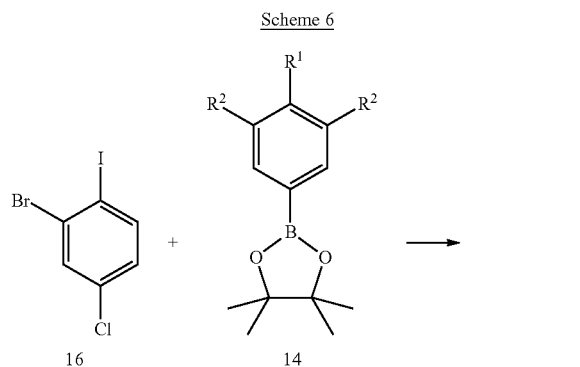

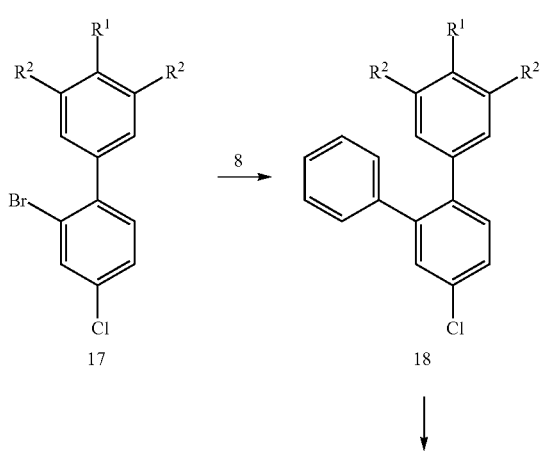

The substituted trisphenylenylboronic acid pinacol ester 19 can be prepared from chlorotrisphenylene 18 and bis(pinacol) ester of 1,4-phenyldiboronic acid under reflux in 1,4-dioxane in the presence of potassium acetate as a base and catalytic amounts of both tris(dibenzylideneacetone)dipalladium(0) ($Pd_2(dba)_3$) and 2-dicyclohexyl-phosphino-2',4',6'-triisopropylbiphenyl (XPhos). Suzuki cross coupling of 19 with 1,3-bis(bromobiphenyl)propan-2-one 13 under reflux in a mixture of toluene, ethanol and water using potassium carbonate as a base and tetrakis(triphenyl-phosphine)palladium(0) yields the substituted 1,3-bis(oligophenylenyl)propan-2-one 8-2.

With the intermediates 3-bromobenzil 4 and the substituted 1,3-bis(oligo-phenylenyl)propan-2-one 8 (m=0, 1 or 2) available, their coupling can be carried out using Knoevenagel condensation (Scheme 7). This can be achieved by reacting 4 and 8 in a mixture of tert-butanol and water at 80° C. in the presence of tetraethylammoniumhydroxid. The obtained substituted 2,5-bis(oligophenylenyl)-3-(3-bromophenyl)-4-phenyl-2,4-cyclopentadienone 20 is further reacted using trimethylsilyl acetylene, bis(triphenylphosphine)palladiumchloride(II) and copper(I) iodide in a Sonogashira cross coupling reaction. This yields substituted 2,5-bis(oligophenylenyl)-3-(3-trimethylsilylacetylphenyl)-4-phenyl-2,4-clopentadienone 21. Using potassium carbonate as base finally results in the formation of oligophenylene monomer of general formula (I). The reaction works well when a 1:1 mixture of THF and methanol is used.

Scheme 7

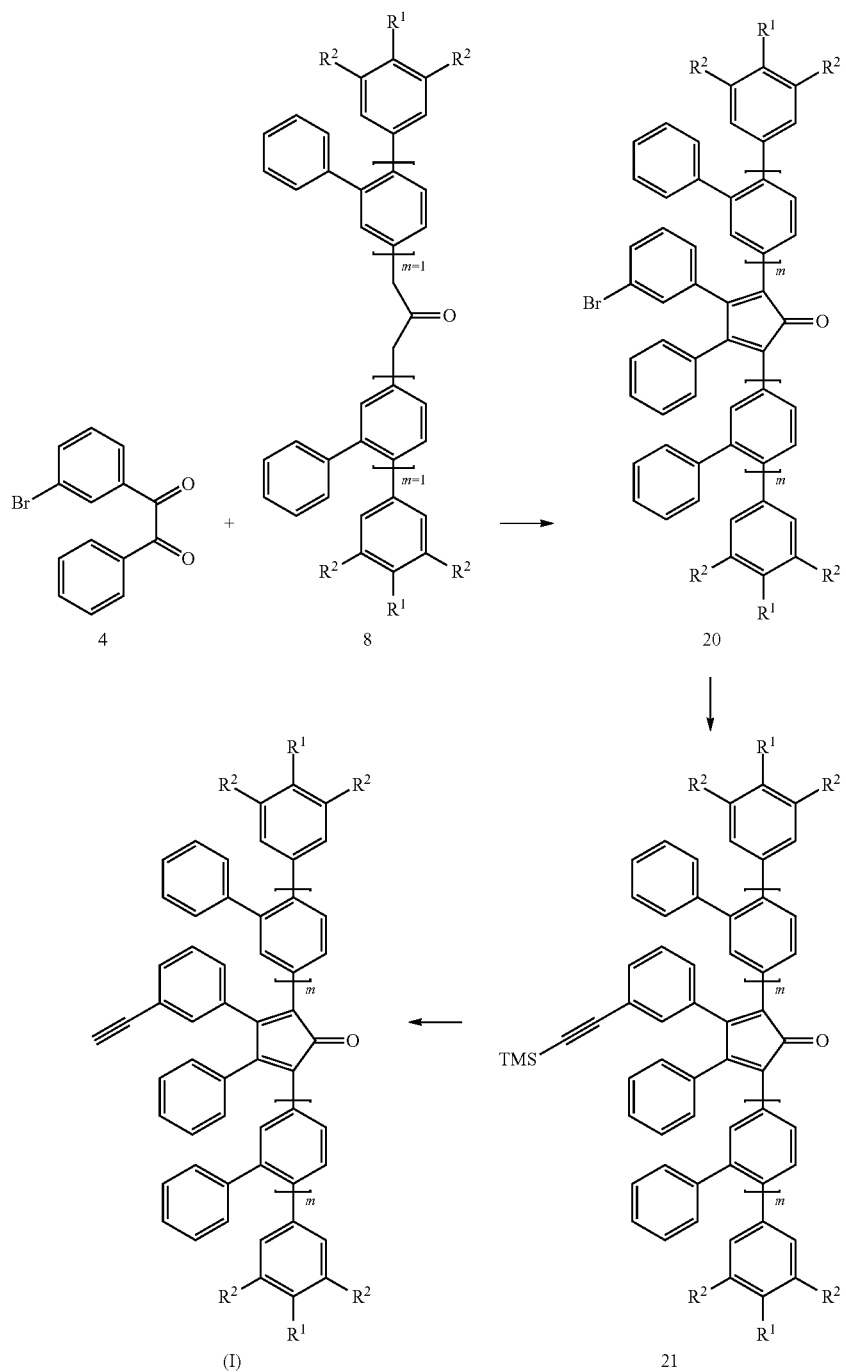

Various articles of manufacture including electronic devices, optical devices, and optoelectronic devices, such as field effect transistors (e.g., thin film transistors), photovoltaics, organic light emitting diodes (OLEDs), complementary metal oxide semiconductors (CMOSs), complementary inverters, D flip-flops, rectifiers, and ring oscillators, that make use of the graphene nanoribbons disclosed herein also are within the scope of the present invention as are methods of making the same.

The present invention, therefore, further provides methods of preparing a semiconductor material. The methods can include preparing a composition that includes one or more of the graphene nanoribbons of the invention disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes one or more of the graphene nanoribbons disclosed herein. In various embodiments, the liquid medium can be an organic solvent, an inorganic solvent such as water, or combinations thereof. In some embodiments, the composition can further include one or more additives independently selected from detergents, dispersants, binding agents, compatibilizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatibilizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, spraying or vacuum filtration.

The present invention further provides articles of manufacture such as the various devices described herein that include a composite having a semiconductor material of the present invention and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2Cl_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., PNAS, 102 (13): 4678-4682 (2005)), as well as hybrid organic/inorganic dielectric materials (e.g., described in US 2007/0181961 A1). The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrene-sulfonate) (PEDOT:PSS), polyaniline (PANI), polypyrrole (PPy). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture, in which graphene nanoribbons of the present invention are useful, are photovoltaics or solar cells. Compounds of the present invention can exhibit broad optical absorption and/or a very positively shifted reduction potential, making them desirable for such applications. Accordingly, the graphene nanoribbons described herein can be used as a n-type semiconductor in a photovoltaic design, which includes an adjacent p-type semiconductor material that forms a p-n junction. The compounds can be in the form of a thin film semiconductor, which can be deposited on a substrate to form a composite. Exploitation of compounds of the present invention in such devices is within the knowledge of a skilled artisan.

Accordingly, another aspect of the present invention relates to methods of fabricating an organic field effect transistor that incorporates a semiconductor material of the present invention. The semiconductor materials of the present invention can be used to fabricate various types of organic field effect transistors including top-gate top-contact capacitor structures, top-gate bottom-contact capacitor structures, bottom-gate top-contact capacitor structures, and bottom-gate bottom-contact capacitor structures.

In certain embodiments, OTFT devices can be fabricated with the present graphene nanoribbons on doped silicon substrates, using $SiO_2$ as the dielectric, in top-contact geometries. In particular embodiments, the active semiconductor layer which incorporates at least a graphene nanoribbon of the present invention can be deposited at room temperature or at an elevated temperature. In other embodiments, the active semiconductor layer which incorporates at least a graphene nanoribbon of the present invention can be applied by spin-coating or printing as described herein. For top-contact devices, metallic contacts can be patterned on top of the films using shadow masks.

The invention is illustrated in more detail by the following examples.

(Tetramer=$C_{216}H_{274}$, exact mass=2868,14, molecular weight=2870,49; pentamer=$C_{270}H_{342}$, exact mass=3584,68; molecular weight=3587,60; hexamer=$C_{324}H_{410}$, exact mass=4301,21, molecular weight=4304,72; heptamer=$C_{378}H_{478}$, exact mass=5017,74, molecular weight=5021,84)

Figure 4:
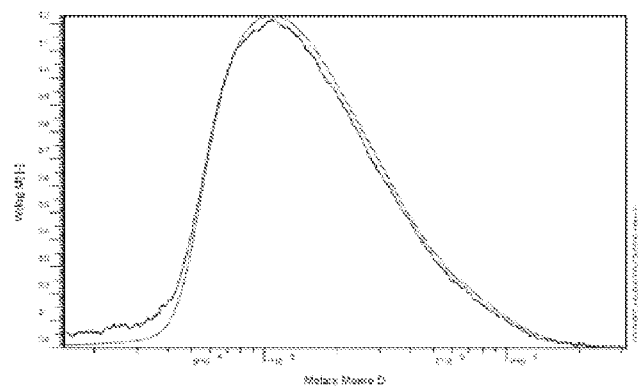

FIG. 4: Molecular weight distribution of polymeric precursor IIa after fractionation by GPC (Table 1, entry 2, THF, PSS).

Figure 5:
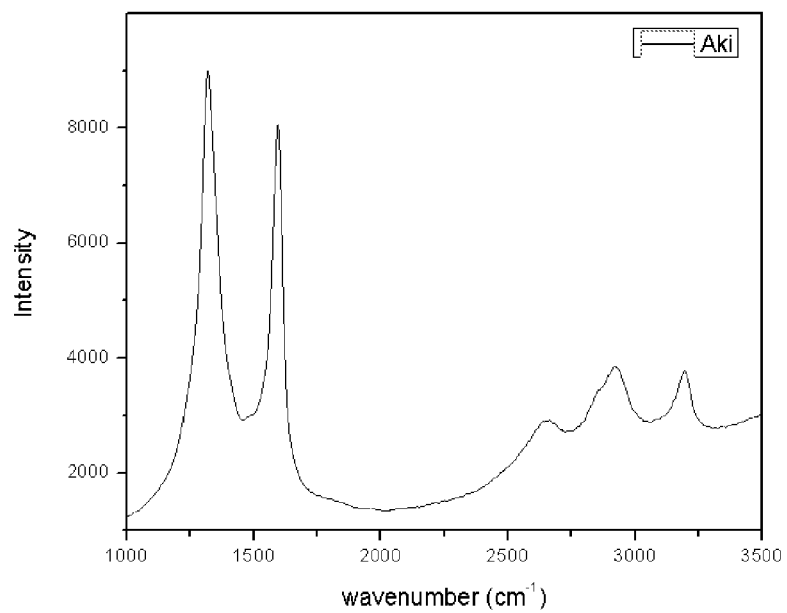

FIG. 5: Raman spectrum of graphene nanoribbons IIIa (powder).

Figure 6:
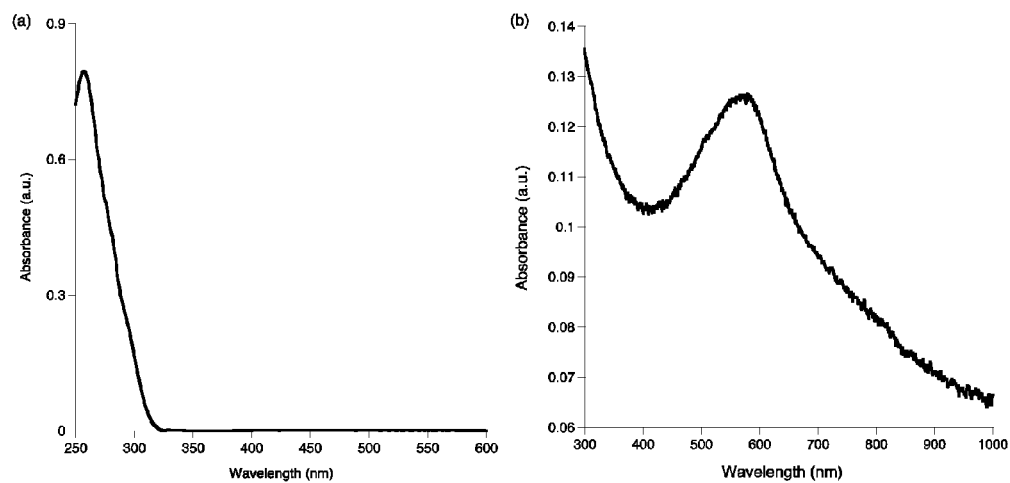

FIG. 6: Comparison of UV-VIS absorption spectra: (a) polymeric precursor IIa in THF (14 µg/mL) and (b) graphene nanoribbons IIIa as a film on a glass substrate drop-casted from dispersion in THF.

Figure 7:
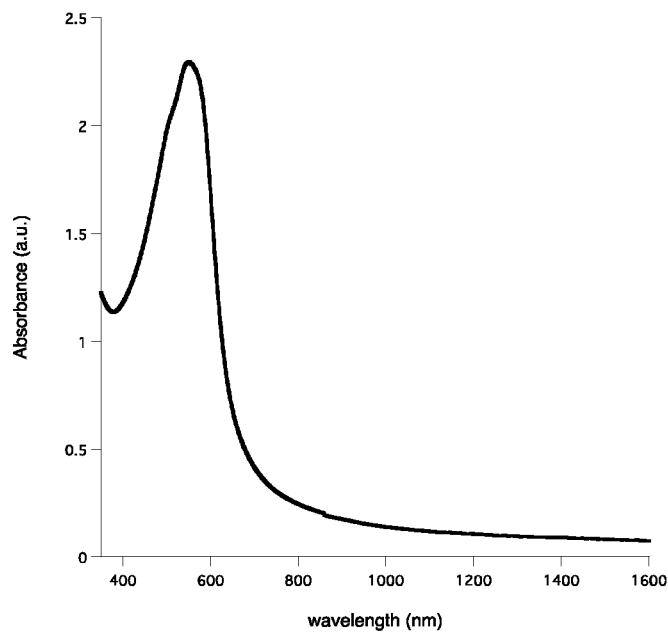

FIG. 7: UV-vis absorption spectrum of graphene nanoribbons IIIa in an exfoliated solution in NMP.

Figure 8:
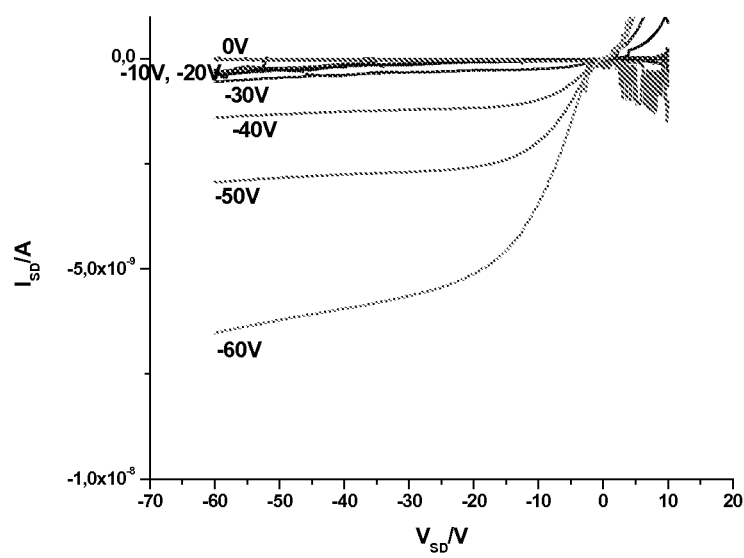

FIG. 8: Output characteristics of graphene nanoribbons IIIa at various gate biases $V_G$ FIG. 9: Transfer curve of graphene nanoribbons IIIa at a source drain bias of $V_{SD}$=-60V.

EXAMPLES

Example 1

Preparation of 3-Bromodiphenylacetylene (3)

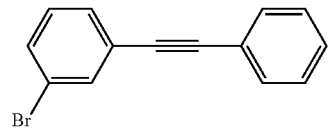 [SMILES: Brc1cccc(C#Cc2ccccc2)c1]

To a degassed solution of 1-bromo-3-iodobenzene 1 (5.03 g, 17.8 mmol) and ethynylbenzene 2 (2.08 g, 20.4 mmol) in a mixture of THF (50 mL) and triethylamine (50 mL) were added copper(I) iodide (52.7 mg, 0.277 mmol) and dichlorobis(triphenylphosphine)palladium(II) (376 mg, 0.536 mmol). After stirring at room temperature for 18 h, the reaction mixture was filtered to remove precipitates. The filtrate was diluted with diethylether, and washed twice with a saturated aqueous solution of ammonium chloride and three times with brine followed by drying over sodium sulfate and concentration in vacuo. Dark brown crude material was purified by silica gel column chromatography (eluent: hexane) to give the title compound as colorless oil (4.46 g, 98% yield).

$^1$H NMR (300 MHz, CD$_2$Cl$_2$): δ 7.25 (t, J=7.9 Hz, 1H), 7.35-7.41 (m, 3H), 7.46-7.57 (m, 4H), 7.70 (t, J=1.7 Hz, 1H).

$^{13}$C NMR (75 MHz, CDCl$_3$): δ 87.77, 90.65, 122.16, 122.73, 125.30, 128.40, 128.61, 129.76, 130.13, 131.36, 131.66, 134.31.

Elemental Analysis: Calc. for C$_{14}$H$_9$Br: C, 65.40; H, 3.53. Found: C, 65.53; H, 3.65.

Example 2

Preparation of 3-Bromobenzil (4)

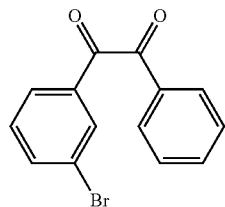 [SMILES: O=C(C(=O)c1cccc(Br)c1)c1ccccc1]

To a solution of 3-bromodiphenylacetylene 3 (6.38 g, 24.8 mmol) in DMSO (60 mL) was added iodine (3.15 g, 12.4 mmol). The reaction mixture was degassed and stirred at 155° C. for 20 h. After cooling down to room temperature, the reaction was quenched with a saturated aqueous solution of sodium sulfite followed by dilution with dichloromethane. The aqueous layer was extracted three times with dichloromethane and the combined organic layers were washed five times with water. After drying over sodium sulfate and concentration in vacuo purification by silica gel column chromatography (eluent: 30-50% dichloromethane/hexane) yielded the title compound as a yellow solid (4.47 g, 62% yield).

$^1$H NMR (300 MHz, CD$_2$Cl$_2$): δ 7.42 (t, J=7.9 Hz, 1H), 7.51-7.59 (m, 2H), 7.71 (tt, J=1.3, 7.4 Hz, 1H), 7.82 (qd, J=0.99, 8.0 Hz, 1H), 7.89 (td, J=1.2, 7.8 Hz, 1H), 7.93-7.98 (m, 2H), 8.13 (t, J=1.8 Hz, 1H).

$^{13}$C NMR (75 MHz, CD$_2$Cl$_2$): δ 123.61, 128.99, 129.53, 130.29, 131.10, 132.79, 133.11, 135.16, 135.59, 138.12, 193.42, 194.08.

Elemental Analysis: Calc. for C$_{14}$H$_9$BrO$_2$: C, 58.16; H, 3.14. Found: C, 58.21; H, 3.32.

Example 3

Preparation of 3-(3-Bromophenyl)-2,5-bis(4-dodecylphenyl)-4-phenyl-2,4-cyclopentadienone (20a)

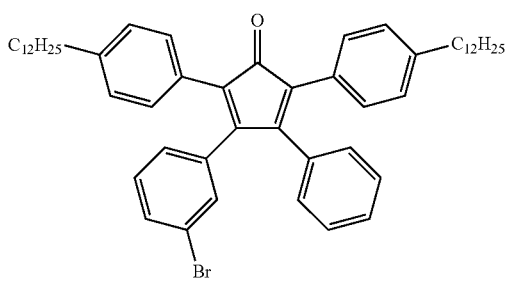

To a solution of 3-bromobenzil 4 (2.00 g, 6.92 mmol) and 1,3-bis(4-dodecylphenyl)-propan-2-one (8a) (3.79 g, 6.93 mmol) in tert-butanol (200 mL) was added at 80° C. an aqueous solution of tetraethylammonium hydroxide (20%, 2.05 mL, 2.77 mmol). After stirring at 80° C. for 50 min the reaction was quenched by the addition of 1 N HCl (40 mL), and the reaction mixture was extracted three times with dichloromethane. The combined organic extracts were washed with water three times, dried over sodium sulfate, and evaporated to give a purple crude product. Purification by silica gel column chromatography (eluent: 20% dichloromethane/hexane) gave the title compound as a purple solid (5.05 g, 91% yield).

$^1$H NMR (300 MHz, CD$_2$Cl$_2$): δ 0.86-0.90 (m, 6H), 1.23-1.37 (m, 36H), 1.51-1.66 (m, 4H), 2.52-2.62 (m, 4H), 6.87-6.92 (m, 1H), 6.93-6.98 (m, 2H), 7.04-7.16 (m, 10H), 7.18-7.32 (m, 3H), 7.35-7.41 (m, 1H).

$^{13}$C NMR (75 MHz, CD$_2$Cl$_2$): δ 14.30 (2C), 23.12 (2C), 29.75 (2C), 29.79 (2C), 29.92 (2C), 30.02 (2C), 30.07 (2C), 30.09 (2C), 30.11 (2C), 31.74 (2C), 32.36 (2C), 36.13 (2C), 122.25, 125.64, 126.36, 128.12, 128.46 (2C), 128.48 (2C), 128.60 (2C), 128.90, 129.60 (2C), 129.97, 130.25, 130.34 (2C), 130.35 (2C), 131.61, 132.46, 133.63, 136.13, 143.13, 143.38, 152.58, 152.63, 154.27, 200.93.

Elemental Analysis: Calc. for C$_{39}$H$_{62}$O: C, 79.57; H, 8.44. Found: C, 79.59; H, 8.56.

Example 4

Preparation of 2,5-Bis(4-dodecylphenyl)-3-phenyl-4-(3-((trimethylsilyl)ethynyl)-phenyl)-2,4-cyclopentadienone (21a)

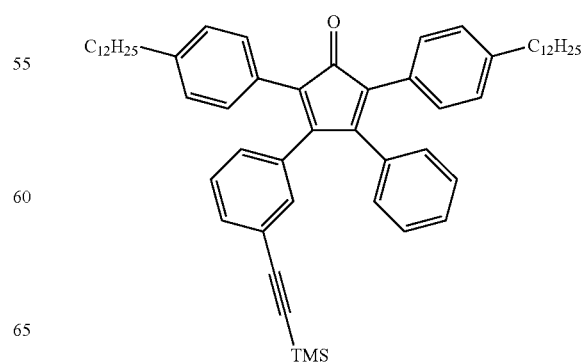

To a degassed suspension of 3-(3-bromophenyl)-2,5-bis (4-dodecylphenyl)-4-phenyl-2,4-cyclopentadienone 20a (3.00 g, 3.75 mmol) and copper(I) iodide (73.5 mg, 0.386 mmol) in triethylamine (200 mL) were added trimethylsilylacetylene (1.60 mL, 11.3 mmol) and tetrakis-(triphenylphosphino)-palladium(0) (438 mg, 0.379 mmol). After stirring at 80° C. for 19 h, the solvent was removed in vacuo. The resulting purple solid was dissolved in dichloromethane and washed once with a saturated aqueous solution of ammonium chloride and then twice with brine. After drying over sodium sulfate and concentration in vacuo, purification by silica gel column chromatography (eluent: 15% dichloromethane/hexane) yielded the title compound as a purple solid (2.10 g, 69% yield).

$^1$H NMR (300 MHz, CD$_2$Cl$_2$): δ 0.19 (s, 9H), 0.88 (t, J=6.7 Hz, 6H), 1.23-1.36 (m, 36H), 1.55-1.65 (m, 4H), 2.52-2.61 (m, 4H), 6.87-6.92 (m, 1H), 6.92-6.97 (m, 2H), 7.04-7.29 (m, 13H), 7.30-7.35 (m, 1H).

$^{13}$C NMR (75 MHz, CD$_2$Cl$_2$): δ 0.10 (3C), 14.30 (2C), 23.12 (2C), 29.78 (2C), 29.82 (2C), 29.91 (2C), 30.01 (2C), 30.07 (4C), 30.10 (2C), 31.75 (2C), 32.35 (2C), 36.14 (2C), 95.25, 104.61, 123.49, 125.52, 126.01, 128.27, 128.41 (2C), 128.47 (2C), 128.53 (2C), 128.67, 128.81, 129.61 (2C), 129.82, 130.34 (4C), 130.61, 132.07, 132.50, 133.70, 134.47, 143.07, 143.28, 153.43, 154.43, 154.27, 201.13.

Elemental Analysis: Calc. for C$_{58}$H$_{76}$OSi: C, 85.23; H, 9.37. Found: C, 84.84; H, 9.33.

Example 5

Preparation of 2,5-Bis(4-dodecylphenyl)-3-(3-ethynylphenyl)-4-phenyl-2,4-cyclopentadienone (Ia)

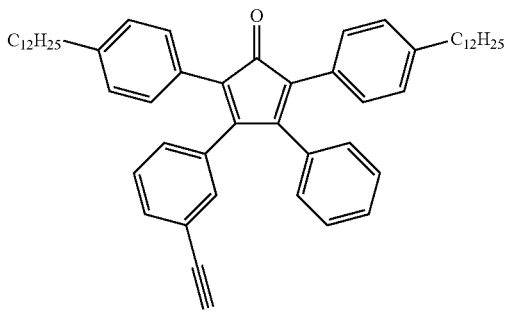

Methanol (100 mL) was added to a suspension of 2,5-bis (4-dodecylphenyl)-3-phenyl-4-(3-((trimethylsilyl)ethynyl) phenyl)-2,4-cyclopentadienone 21a (1.02 g, 1.25 mmol) and potassium fluoride (361 mg, 6.21 mmol) in THF (100 mL), and the reaction mixture was stirred at 40° C. for 5 h. After removal of the solvents at 40° C. in vacuo, purification by silica gel column chromatography (eluent: 15% dichloromethane/hexane) yielded the title compound as a purple solid (786 mg, 84% yield).

$^1$H NMR (300 MHz, CD$_2$Cl$_2$): δ 0.88 (t, J=6.7 Hz, 6H), 1.23-1.36 (m, 36H), 1.51-1.65 (m, 4H), 2.51-2.61 (m, 4H), 3.04 (s, 1H), 6.91-6.97 (m, 3H), 7.04-7.30 (m, 13H), 7.35-7.39 (m, 1H).

$^{13}$C NMR (75 MHz, CD$_2$Cl$_2$): δ 14.33 (2C), 23.14 (2C), 29.80 (4C), 29.93 (2C), 30.03 (2C), 30.09 (4C), 30.12 (2C), 31.75 (2C), 32.37 (2C), 36.14 (2C), 77.93, 83.22, 122.35, 125.61, 126.17, 128.25, 128.44 (2C), 128.48 (2C), 128.52, 128.54, 128.56 (2C), 128.84, 129.63 (2C), 130.19, 130.36 (4C), 132.28, 133.00, 133.69, 134.44, 143.08, 143.27, 153.21, 154.34, 201.06.

HRMS (ESI, positive) m/z calc. for C$_{55}$H$_{69}$O [M+H]$^+$ 745.5348, found 745.5334.

Example 6

Preparation of Polymeric Precursor (IIa)

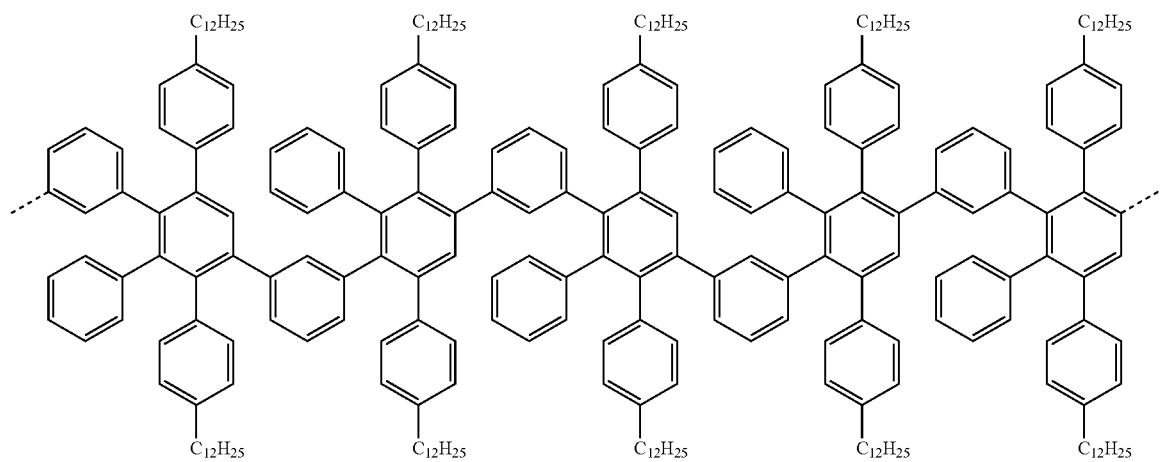

Method 1: Diels-Alder-Polymerization in a Solution of Diphenyl Ether

A degassed solution of 2,5-bis(4-dodecylphenyl)-3-(3-ethynylphenyl)-4-phenyl-2,4-cyclopentadienone Ia in diphenyl ether was refluxed using a heating mantle. After cooling down to room temperature, diphenyl ether was distilled off and the resulting crude material was fractionated by using recycling gel permeation chromatography (GPC) system (eluent: chloroform).

$^1$H NMR (300 MHz, $CD_2Cl_2$): δ 0.81-0.92 (m, 6H), 1.00-1.68 (m, 40H), 2.15-2.75 (m, 4H), 6.15-7.38 (m, 18H).

Method 2: Diels-Alder-Polymerization in a Neat Condition

A purple powder of 2,5-bis(4-dodecylphenyl)-3-(3-ethynylphenyl)-4-phenyl-2,4-cyclopentadienone Ia in a 25-mL Schlenk tube was heated to 260° C. using a heating mantle. The powder at first melted and then lost its purple color to be pale yellow. After cooling down to room temperature, the resulting polymer was sonicated in THF for 30 min, and the insoluble polymer was filtered off. The filtrate was concentrated in vacuo and fractionated by gel permeation chromatography (eluent: dichloromethane).

TABLE 1

Reaction conditions and the resulting molecular weights of polymeric precursor IIa

| entry | solvent | concentration (mM) | time (h) | $M_w$ (g/mol)$^a$ |
|---|---|---|---|---|
| 1 | $Ph_2O$ | 36.6 | 25 | 24000 |
| 2 | $Ph_2O$ | 228 | 28 | 150000 |
| 3 | neat | — | 1.5 | 350000$^b$ |
| 4 | neat | — | 5 | 620000$^b$ |

$^a$GPC analysis of the crude products (THF, PSS, UV detector)
$^b$Crude products were extracted from unsoluble polymer with THF using sonication.

Figure 1:
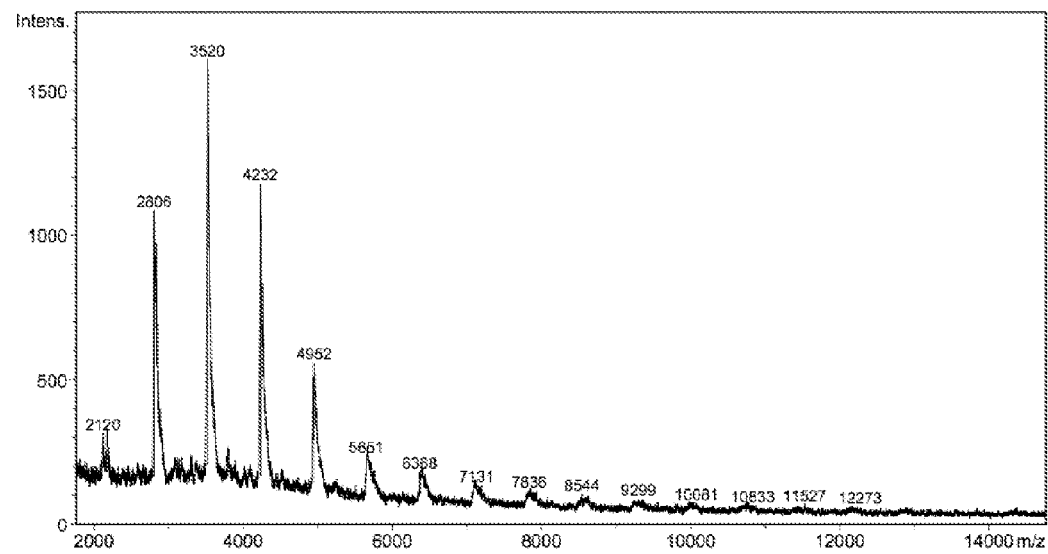
FIG. 1: MALDI-TOF MS analysis of a crude product of polymeric precursor IIa (Table 1, entry 1, matrix: TCNQ, linear mode).
Figure 2:
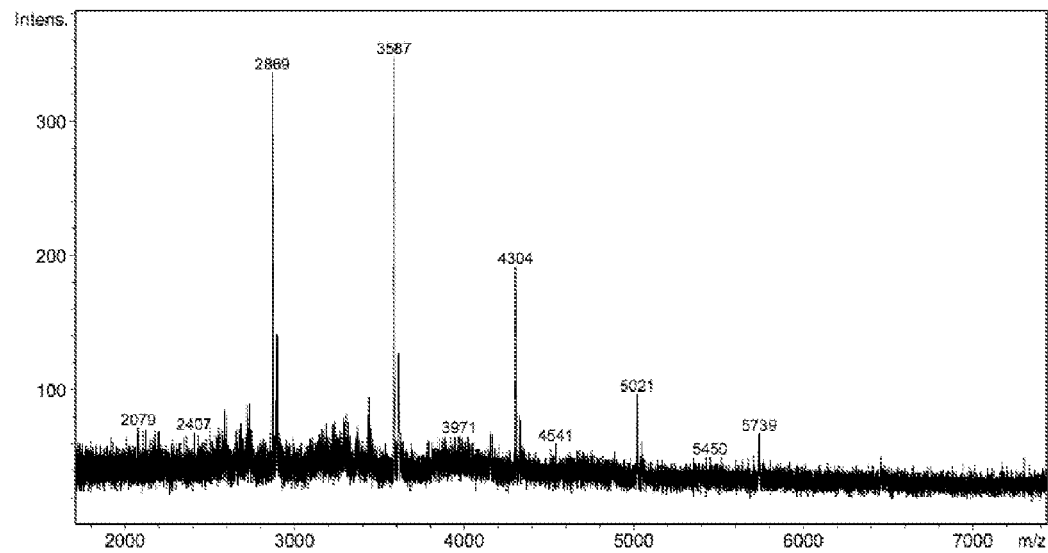
FIG. 2: MALDI-TOF MS analysis of a crude product of polymeric precursor IIa (Table 1, entry 1, matrix: TCNQ, reflectron mode).
Figure 3:
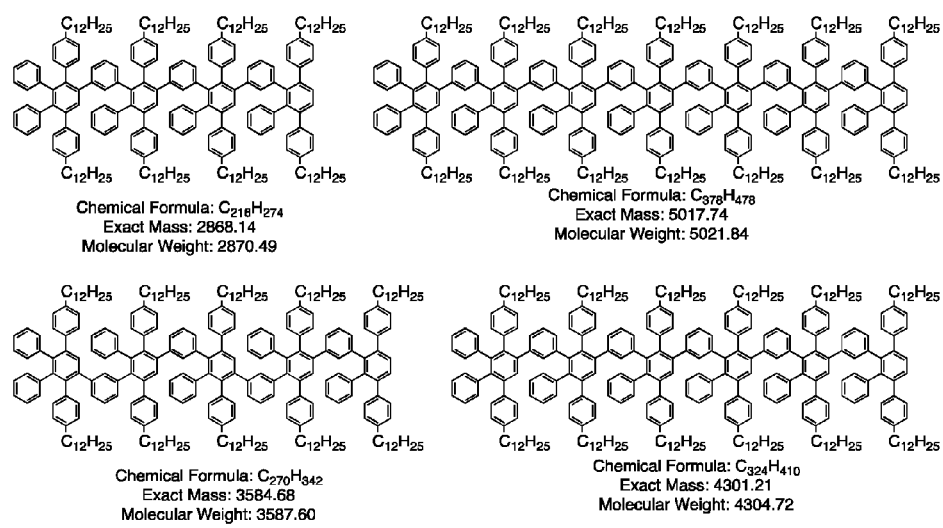
FIG. 3: Chemical formulae, exact masses and molecular weights of tetrameric, pentameric, hexameric and heptameric polymeric precursor IIa.

MALDI analysis of a crude product of polymeric precursor IIa (Table 1, entry 1) in reflectron mode showed peaks of tetramer, pentamer, hexamer, heptamer, and octamer at 2869, 3587, 4304, 5021, and 5739, respectively, which indicated that the ethynyl groups and tetraphenylcyclopentadienone moieties at the edges of them was reacted during the reaction (FIG. 2).

Example 7

Preparation of Graphene Nanoribbons (IIIa)

A solution of polymeric precursor IIa in non-stabilized dichloromethane was degassed by argon bubbling for 10 min. To the degassed solution was added a suspension of iron(III) chloride in nitromethane. After stirring at room temperature for 3 days under continuous argon bubbling, the reaction was quenched by the addition of methanol to form black precipitates. Filtration by suction using a membrane filter and washing with methanol gave the title compound as black powder.

Although the solubility of graphene nanoribbons IIIa in normal organic solvents was very poor, it was possible to disperse IIIa in THF with the help of sonication. Analysis of the dispersion was not possible because it started to reaggregate immediately after stopping the sonication, but it was possible to make a film of IIIa by drop-casting it on glass substrate and measure solid-state UV-VIS absorption spectrum (FIG. 6b). It was demonstrated that the absorption band is dramatically red shifted upon the cyclodehydrogenation of polymeric precursor IIa (FIG. 6a) to graphene nanoribbons IIIa (FIG. 6b). The spectrum of graphene nanoribbons IIIa showed an absorption peak at 570 nm.

Exfoliation of graphene nanoribbons IIIa was performed in NMP with the help of sonication, which gave UV-VIS absorption spectrum of IIIa from exfoliated solution (FIG. 7). An absorption peak was observed at 550 nm.

Figure 9:
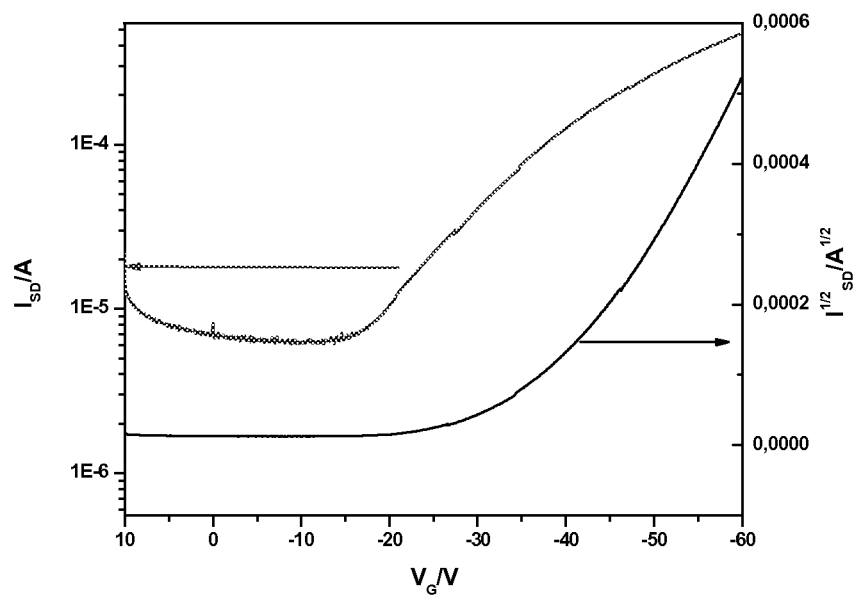

Fabrication of OFET devices with graphene nanoribbons IIIa was performed by drop casting the dispersion of IIIa in THF directly after sonication, which demonstrates the field-effect mobility of graphene nanoribbons IIIa to be $\mu_{max}$=0.001 cm$^2$/vs and $\mu_{avg}$=0.00087 cm$^2$/vs in HMDS modified OFET devices (FIGS. 8 and 9).

Example 8

Preparation of 1,3-Bis(4-(2-decyltetradecyl)phenyl) propan-2-one (8b)

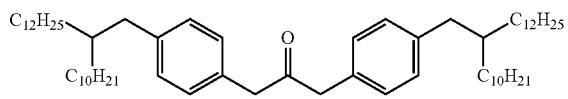

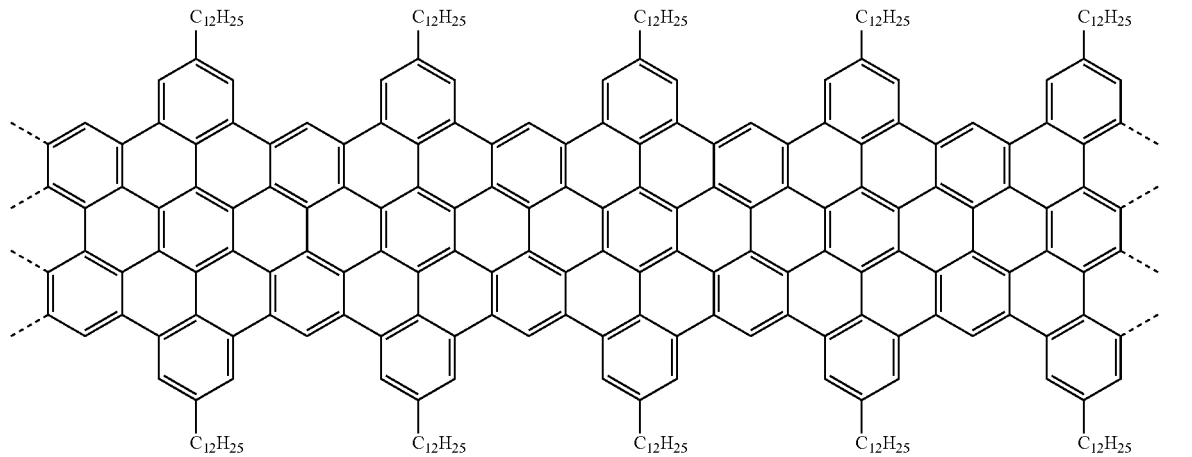

Dry N,N-dimethylacetamide (10 mL) was added to zinc (3.21 g, 49.1 mmol) and iodine (0.689 mg, 2.71 mmol) in a 100-mL two-necked flask equipped with a condenser, and stirred at room temperature until the purple color of iodine disappeared. 2-decyl-tetradecylbromide (15.3 g, 36.7 mmol) was then added to the mixture and stirred at 80° C. for 24 h to generate dodecylzinc bromide. To 1,3-bis(4-bromophenyl)-propan-2-one 7b (2.00 g, 5.43 mmol) and dichloro[1,1'-bis(diphenylphosphino)-ferrocene]palladium(II) (0.384 g, 0.544 mmol) in a 100-mL Schlenk flask was added via cannula the solution of dodecylzinc bromide. The reaction mixture was stirred at room temperature for 18 h, and then quenched by hydrochloric acid (2 M, 40 mL). The aqueous layer was extracted three times with dichloromethane. The combined organic extracts were washed three times with water, dried over sodium sulfate, and evaporated. The crude material was purified by silica gel column chromatography (eluent: 20% dichloromethane/hexane) to give the title compound as pale yellow oil (4.13 g, 86% yield).

$^1$H NMR (300 MHz, CD$_2$Cl$_2$) □: δ 0.88 (t, J=6.7 Hz, 12H), 1.16-1.37 (m, 80H), 1.55-1.67 (m, 2H), 2.50 (d, J=7.0 Hz, 4H), 3.68 (s, 4H), 7.01 (d, J=8.1 Hz, 4H), 7.09 (d, J=8.1 Hz, 4H).

$^{13}$C NMR (75 MHz, CD$_2$Cl$_2$): δ 14.36 (4C), 23.18 (4C), 26.99 (4C), 29.85 (4C), 30.16 (16C), 30.50 (4C), 32.42 (4C), 33.60 (4C), 40.12 (2C), 40.57 (2C), 49.13 (2C), 129.70 (4C), 129.86 (4C), 131.88 (2C), 141.11 (2C), 206.30.

Elemental Analysis: Calc. for C$_{63}$H$_{110}$O: C, 85.64; H, 12.55. Found: C, 85.71; H, 12.45.

Example 9

Preparation of 3-(3-Bromophenyl)-2,5-bis(4-(2-decyltetradecyl)phenyl)-4-phenyl-2,4-cyclopentadienone (20b)

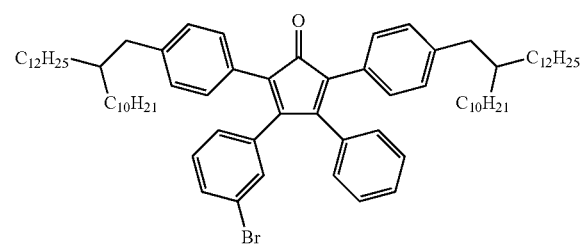

To a solution of 3-bromobenzil 4 (0.808 g, 2.79 mmol) and 1,3-bis(4-(2-decyltetradecyl)phenyl)propan-2-one 8b (2.55 g, 2.89 mmol) in tert-butanol (70 mL) was added at 80° C. an aqueous solution of tetraethylammonium hydroxide (20%, 0.82 mL, 1.12 mmol). After stirring at 80° C. for 40 min, the reaction was quenched by the addition of hydrochloric acid (2 M, 20 mL), and the reaction mixture was concentrated in vacuo and then extracted twice with dichloromethane. The combined organic extracts were washed twice with water, dried over sodium sulfate, and evaporated. Purification by silica gel column chromatography (eluent: 10% dichloromethane/hexane) gave the title compound as a purple oil (2.71 g, 85% yield).

$^1$H NMR (300 MHz, CD$_2$Cl$_2$): δ 0.88 (t, J=6.7 Hz, 12H), 1.15-1.35 (m, 80H), 1.55-1.67 (m, 2H), 2.50 (t, J=6.4 Hz, 4H), 6.87 (td, J=1.1, 7.9 Hz, 1H), 6.92-6.98 (m, 2H), 7.01-7.16 (m, 10H), 7.18-7.32 (m, 3H), 7.35-7.41 (m, 1H).

$^{13}$C NMR (75 MHz, CD$_2$Cl$_2$): δ 14.33 (4C), 23.15 (4C), 26.96 (4C), 29.82 (4C), 30.12 (16C), 30.44 (4C), 32.39 (4C), 33.61 (2C), 33.64 (2C), 40.01 (2C), 40.78 (2C), 122.26, 125.69, 126.42, 128.09, 128.42, 128.47 (2C), 128.49, 128.91, 129.30 (2C), 129.41 (2C), 129.65 (2C), 129.93, 130.20 (4C), 131.62, 132.56, 133.66, 136.13, 142.12, 142.39, 152.55, 154.22, 200.95.

HRMS (ESI, positive) m/z calc. for C$_{77}$H$_{116}$OBr [M+H]$^+$ 1135.8210, found 1135.8199.

Example 10

Preparation of 2,5-Bis(4-(2-decyltetradecyl)phenyl)-3-phenyl-4-(3-((trimethylsilyl)-ethynyl)phenyl-2,4-cyclopentadienone (21b)

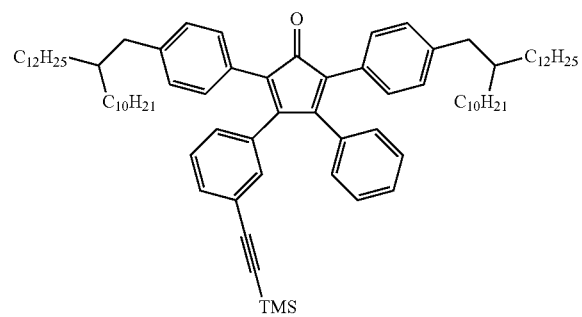

To a degassed suspension of 3-(3-bromophenyl)-2,5-bis (4-(2-decyltetradecyl)phenyl)-4-phenyl-2,4-cyclopentadienone 20b (1.53 g, 1.34 mmol) and copper(I) iodide (30.0 mg, 0.158 mmol) in triethylamine (100 mL) were added trimethylsilylacetylene (0.580 mL, 4.07 mmol) and tetrakis-(triphenylphosphino)-palladium(0) (158 mg, 0.137 mmol). After stirring at 80° C. for 16 h, the solvent was removed in vacuo. Purification by silica gel column chromatography (eluent: 10% dichloromethane/hexane) yielded the title compound as a purple oil (1.23 g, 79% yield).

$^1$H NMR (300 MHz, CD$_2$Cl$_2$): δ 0.19 (s, 9H), 0.88 (t, J=6.8 Hz, 12H), 1.16-1.36 (m, 80H), 1.53-1.66 (m, 2H), 2.45-2.53 (m, 4H), 6.85-6.97 (m, 3H), 7.00-7.29 (m, 13H), 7.30-7.35 (m, 1H).

$^{13}$C NMR (75 MHz, CD$_2$Cl$_2$): δ 0.05 (3C), 14.35 (4C), 23.16 (4C), 26.93 (2C), 26.97 (2C), 29.83 (4C), 30.13 (16C), 30.44 (4C), 32.40 (4C), 33.60 (2C), 33.66 (2C), 39.95, 40.02, 40.71, 40.80, 95.23, 104.66, 123.55, 125.55, 126.02, 128.25, 128.41 (2C), 128.49, 128.52, 128.83, 129.30 (2C), 129.37 (2C), 129.68 (2C), 129.85, 130.21 (4C), 132.10, 132.55, 133.75, 134.55, 142.07, 142.24, 153.42, 154.43, 201.17.

HRMS (ESI, positive) m/z calc. for $C_{83}H_{124}ONaSi$ [M+Na]$^+$ 1175.9319, found 1175.9371.

Example 11

Preparation of 2,5-Bis(4-(2-decyltetradecyl)phenyl)-3-(3-ethynylphenyl)-4-phenyl-2,4-cyclopentadienone (Ib)

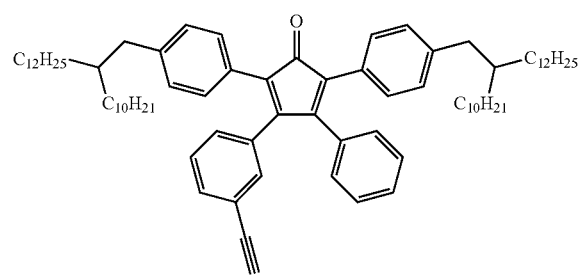

$^1$H NMR (300 MHz, $CD_2Cl_2$): δ 0.88 (t, J=6.8 Hz, 12H), 1.18-1.34 (m, 80H), 1.54-1.67 (m, 2H), 2.46-2.54 (m, 4H), 3.03 (s, 1H), 6.90-6.97 (m, 3H), 7.01-7.30 (m, 13H), 7.34-7.39 (m, 1H).

$^{13}$C NMR (75 MHz, $CD_2Cl_2$): δ 14.32 (4C), 23.13 (4C), 26.93 (4C), 29.80 (4C), 30.10 (16C), 30.41 (4C), 32.37 (4C), 33.58 (2C), 33.62 (2C), 39.98 (2C), 40.75 (2C), 77.87, 83.20, 122.34, 125.63, 126.19, 128.19, 128.40 (2C), 128.46, 128.50, 128.83, 129.28 (2C), 129.36 (2C), 129.66 (2C), 130.19 (5C), 132.26, 133.06, 133.69, 134.43, 142.07, 142.25, 153.18, 154.29, 201.09.

MS (MALDI-TOF) m/z (%) calc. for $C_{79}H_{116}O$ 1081 (43), 1082 (37), 1083 (16), 1084 (4). found 1081 (34), 1082 (38), 1083 (21), 1084 (7).

Example 12

Preparation of Polymeric Precursor (IIb)

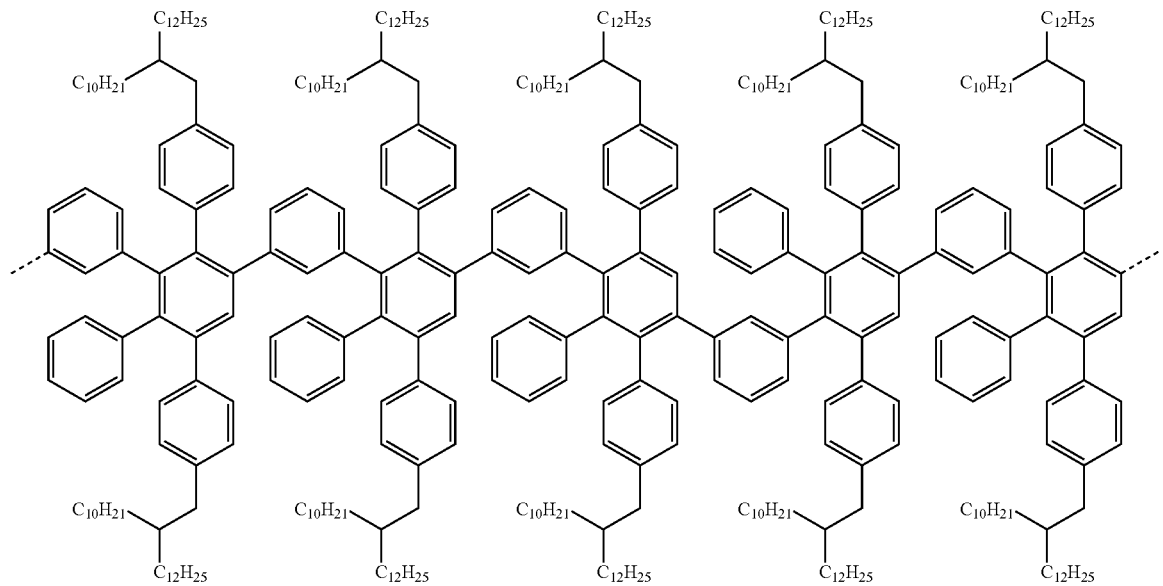

B11/72615PC

Methanol (15 mL) was added to a suspension of 2,5-bis(4-(2-decyltetradecyl)phenyl)-3-phenyl-4-(3-((trimethylsilyl)ethynyl)phenyl-2,4-cyclopentadienone 21b (110 mg, 0.0953 mmol) and potassium fluoride (54.5 mg, 0.938 mmol) in THF (15 mL), and the reaction mixture was stirred at 40° C. for 21 h. After removal of the solvent at 40° C. in vacuo, purification by silica gel column chromatography (eluent: 6-10% dichloromethane/hexane) yielded the title compound as a purple oil (93.8 mg, 91% yield).

A degassed solution of 2,5-bis(4-(2-decyltetradecyl)phenyl)-3-(3-ethynylphenyl)-4-phenyl-2,4-cyclopentadienone (Ib) in a 25-mL Schlenk tube was heated to 260° C. using a heating mantle. The powder at first melted and then lost its purple color to be pale yellow. After cooling down to room temperature the resulting polymer was sonicated in THF for 30 min, and the insoluble polymer was filtered off. The filtrate was concentrated in vacuo and fractionated by gel permeation chromatography (eluent: dichloromethane).

Example 13

Preparation of Graphene Nanoribbons (IIIb)

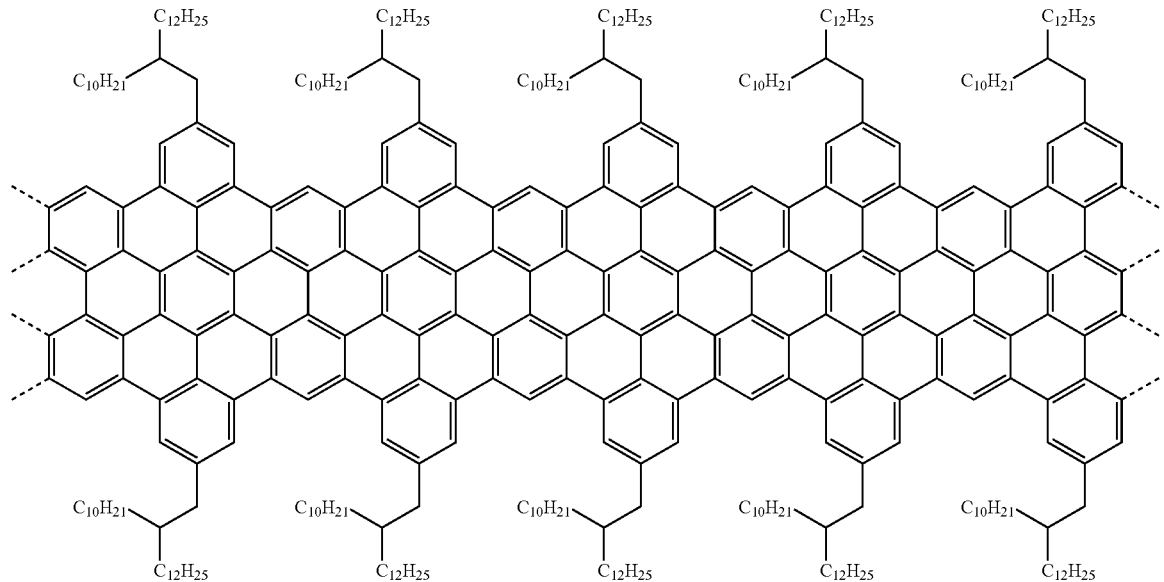

A solution of polymeric precursor IIb in unstabilized dichloromethane was degassed by argon bubbling for 10 min. To the degassed solution was added a suspension of iron(III) chloride in nitromethane. After stirring at room temperature for 3 days under continuous argon bubbling, the reaction was quenched by the addition of methanol to form black precipitates. Filtration by suction using a membrane filter and washing with methanol gave the title compound as black powder.

The invention claimed is:

1. An oligophenylene monomer of general formula (I):

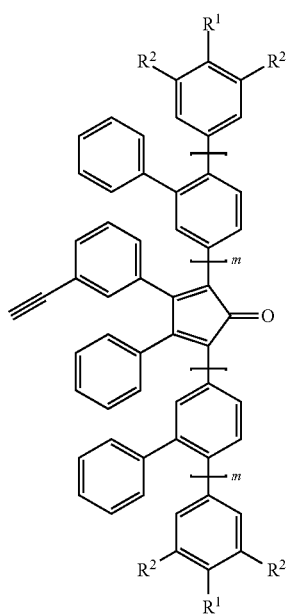

(I)

wherein
$R^1$ is a linear or branched $C_1$-$C_{30}$ alkyl and $R^2$ is H; and
m represents 0, 1 or 2.

2. The oligophenylene monomer of claim 1, wherein each $R^1$ represents a methyl, ethyl, n-propyl, isopropyl, n-butyl, sec.-butyl, isobutyl, tert-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl, or pentacosyl group.

3. The oligophenylene monomer of claim 1, wherein m represents 0.

4. A polymeric precursor for preparing graphene nanoribbons having repeating units of general formula (II):

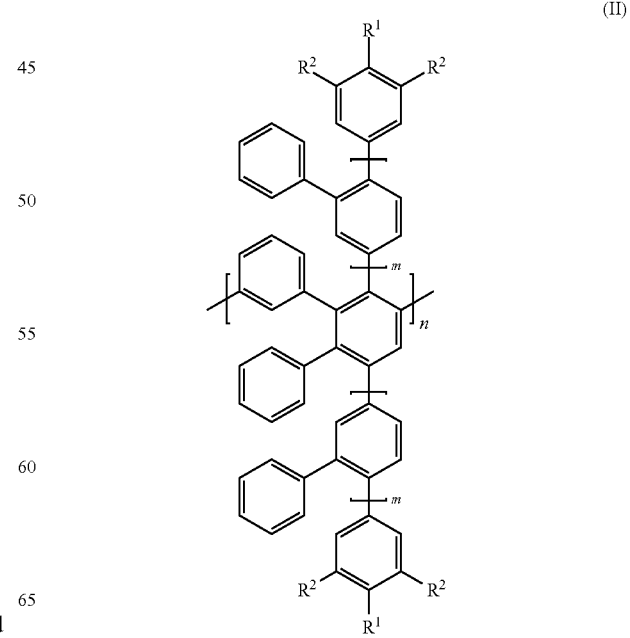

(II)

wherein
R¹ is a linear or branched $C_1$-$C_{30}$ alkyl and R² is H;
m represents 0, 1 or 2; and
n represents a number of from 2 to 100.

5. The polymeric precursor of claim 4, wherein each R¹ represents a methyl, ethyl, n-propyl, isopropyl, n-butyl, sec.-butyl, isobutyl, tert-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl, or pentacosyl group.

6. The polymeric precursor of claim 4, wherein m represents 0.

7. A process for the production of a graphene nanoribbon, comprising: subjecting the polymeric precursor of claim 4 to cyclodehydrogenation.

8. The process of claim 7, wherein the polymeric precursor is prepared by Diels-Alder polymerization of an oligophenylene monomer of general formula (I):

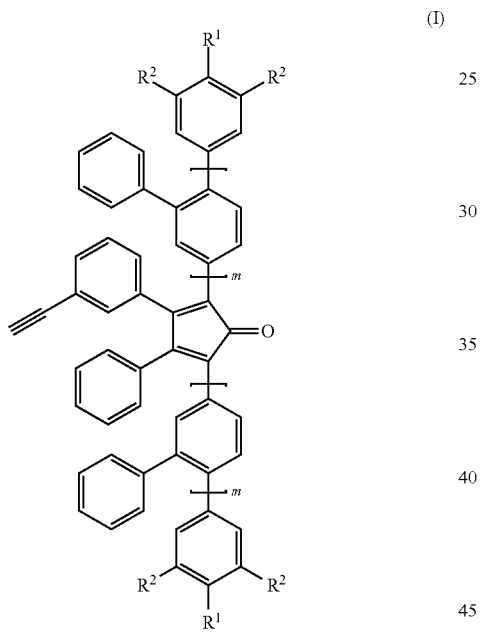

(I)

wherein
R¹ is a linear or branched $C_1$-$C_{30}$ alkyl and R² is H; and
m represents 0, 1 or 2.

9. A graphene nanoribbon, comprising cyclodehydrogenated moieties of formula (II):

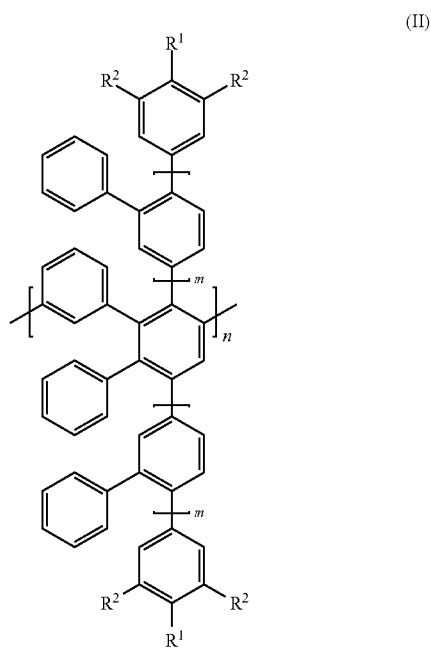

(II)

wherein
R¹ is a linear or branched $C_1$-$C_{30}$ alkyl and R² is H;
m represents 0, 1 or 2; and n represents a number of from 2 to 100.

10. A composition comprising one or more graphene nanoribbons of claim 9 dissolved or dispersed in a liquid medium.

11. An electronic, optical, or optoelectronic device comprising a thin film semiconductor comprising one or more graphene nanoribbons of claim 9.

12. The device of claim 11, wherein the device is an organic field effect transistor device, an organic photovoltaic device, or an organic light-emitting diode.

* * * * *